US008584504B2

(12) United States Patent
Ito et al.

(10) Patent No.: US 8,584,504 B2
(45) Date of Patent: Nov. 19, 2013

(54) AMMONIA CONCENTRATION DETECTION SENSOR

(75) Inventors: Takashi Ito, Kasugai (JP); Sang Jae Lee, Ama-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 423 days.

(21) Appl. No.: 12/835,946

(22) Filed: Jul. 14, 2010

(65) Prior Publication Data

US 2011/0011152 A1 Jan. 20, 2011

(30) Foreign Application Priority Data

Jul. 17, 2009 (JP) ................................. 2009-169292
Jul. 8, 2010 (JP) ................................. 2010-155899

(51) Int. Cl.
*G01N 1/24* (2006.01)
*G01N 27/26* (2006.01)

(52) U.S. Cl.
USPC .......................................... 73/23.2; 204/431

(58) Field of Classification Search
USPC .................................... 73/23.3, 23.2; 204/431
See application file for complete search history.

(56) References Cited

U.S. PATENT DOCUMENTS

| 4,253,302 | A | * | 3/1981 | Asano et al. ..................... 60/276 |
| 5,707,504 | A | | 1/1998 | Jyouno et al. |
| 6,342,140 | B1 | * | 1/2002 | Weyl et al. ..................... 204/424 |
| 7,493,796 | B2 | * | 2/2009 | Wilde .......................... 73/23.31 |
| 7,921,692 | B2 | * | 4/2011 | Isomura et al. .............. 73/23.31 |
| 2004/0118703 | A1 | | 6/2004 | Wang et al. |
| 2006/0108222 | A1 | | 5/2006 | Yamada et al. |
| 2007/0251823 | A1 | | 11/2007 | Yamada |
| 2009/0011252 | A1 | * | 1/2009 | Stein et al. .................... 428/446 |
| 2009/0211906 | A1 | * | 8/2009 | Sugaya et al. ................ 204/424 |
| 2009/0301878 | A1 | * | 12/2009 | Wang et al. .................... 204/429 |
| 2011/0048970 | A1 | * | 3/2011 | Sugaya et al. ................ 205/781 |

FOREIGN PATENT DOCUMENTS

| EP | 2 184 601 A2 | 5/2010 |
| JP | 2004-020313 A1 | 1/2004 |
| JP | 2004-301579 A1 | 10/2004 |
| JP | 2008-191043 A1 | 8/2008 |
| JP | 2009-236556 A1 | 10/2009 |

* cited by examiner

*Primary Examiner* — Peter Macchiarolo
*Assistant Examiner* — Tamiko Bellamy
(74) *Attorney, Agent, or Firm* — Burr & Brown

(57) ABSTRACT

An ammonia concentration detection sensor 100, has: a sensor element 110 capable of detecting the ammonia concentration of a measurement target gas; and a protective cover 120 that regulates the inflow of the measurement target gas into the sensor element 110 and protects the sensor element 110. The protective cover 120 is coated with a coating layer.

3 Claims, 7 Drawing Sheets

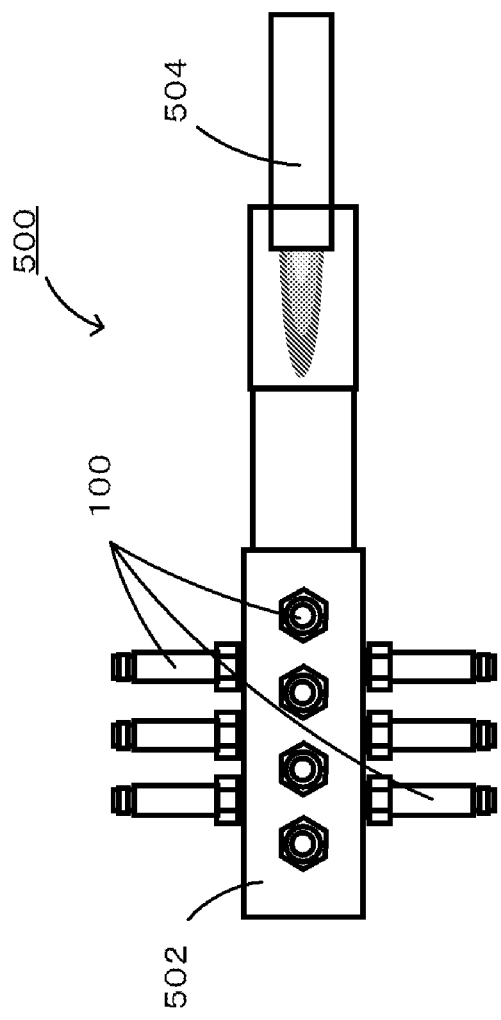
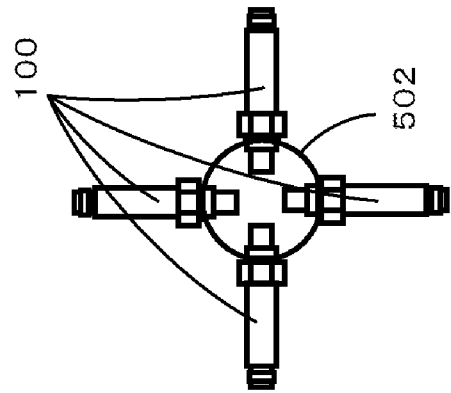

AMMONIA CONCENTRATION DETECTION SENSOR

BACKGROUND OF THE INVENTION

1. Field of the Invention

The present invention relates to an ammonia concentration detection sensor.

2. Description of the Related Art

In recent emission control, it has been examined to introduce a certain reducing agent into exhaust gas before reduction treatment from the outside as required as a method for promoting the reduction of $NO_x$ because ingredients (CO, HC, and the like) for reducing $NO_x$ are insufficient in the exhaust gas of diesel engines. As such a reducing agent, urea has been examined. As the reduction of $NO_x$ by urea, $NO_x$ is reduced by a catalyst utilizing ammonia generated by hydrolyzing urea, and decomposed into harmless $N_2$ and $H_2O$. Here, in order to control the amount of urea to be hydrolyzed, it is necessary to monitor the concentration of ammonia that has been left in an excessive amount after reducing $NO_x$, and thus a sensor therefor is required. As such a sensor, a gas concentration detection sensor can be utilized that detects the concentration of combustible gas ingredients using an oxygen ion conductor. Such a gas concentration detection sensor has been proposed to have a protective cover that is configured to make the flow of exhaust gas uniform or a protective cover that is configured to prevent the adhesion of condensed water generated when starting the engine around a sensor element unit (e.g., Patent Document 1).

Patent Document 1: Japanese Unexamined Patent Application Publication No. 2004-301579

SUMMARY OF INVENTION

However, when the ammonia concentration is detected using the gas concentration detection sensor provided with the protective cover, it has been proved that the detection sensitivity decreases with time.

The present invention has been made in order to solve the problem. It is a primary object of the invention to provide an ammonia concentration detection sensor whose ammonia concentration detection sensitivity is hard to decrease even when used over a long period of time.

When the present inventors removed the protective cover of the gas concentration detection sensor whose sensitivity decreased with time and detected the ammonia concentration again, the sensitivity recovered. Thus, the present inventors have considered that the sensor element unit did not deteriorate but the protective cover deteriorated with time, and ammonia was decomposed by the protective cover after deterioration with time, and the sensitivity decreased. Although the mechanism in which ammonia is decomposed by the protective cover after deteriorating with time is not clear, the mechanism is imagined as follows, for example. More specifically, a mechanism is imagined in which there is a possibility that the protective cover contains reaction substances that react with ammonia, and minute irregularities (roughness) arise on the surface due to oxidization of the protective cover to increase reaction sites of ammonia and the reaction substances contained in the protective cover. Or, a mechanism is also imagined in which the radiant heat in the protective cover increases due to the deterioration with time of the protective cover to increase the temperature, and thus the reaction of ammonia and the reaction substances contained in the protective cover is accelerated. In view of the above, the present inventors coated the protective cover with a coating layer. Then, the present inventors have found that a reduction in the sensitivity with time is suppressed. Thus, the present invention has been accomplished.

More specifically, the ammonia concentration detection sensor of the present invention is an ammonia concentration detection sensor having a sensor element capable of detecting the ammonia concentration of a measurement target gas and a protective cover that regulates the inflow of the measurement target gas to the sensor element and protects the sensor element, in which the protective cover is coated with a coating layer.

In the ammonia concentration detection sensor, since the protective cover is coated with the coating layer, the protective cover is hard to deteriorate even when exposed to an oxidative gas or a corrosive gas over a long period of time. Thus, even when the ammonia concentration detection sensor is used over a long period of time, the ammonia concentration detection sensitivity is hard to decrease.

In the ammonia concentration detection sensor of the present invention, the protective cover is formed of stainless steel and the coating layer is a nitride, a carbide, or a carbonitride of a metal element and may contain at least one member selected from the group consisting of Ti, Zr, and Cr as the metal element. The coating layer is preferably hydrophobic. Thus, water is difficult to adhere to the protective cover, and thus the formation of cracks due to the adhesion of water to the sensor element can be prevented. As such a coating layer, TiC, TiCN, TiN, ZrC, ZrCN, ZrN, CrC, CrCN, CrN, TiAlN, ZrAlN, CrAlN, and the like are mentioned. The coating layer preferably has a heat resistant temperature of 400° C. or higher. Thus, since the temperature of the protective cover is 250° C. or lower at a usual operation temperature of the sensor element (700° C. or higher), the deterioration of the protective cover can be favorably prevented.

In an exhaust system in which a nitrogen oxide is generated, the ammonia concentration detection sensor of the present invention may be disposed before and/or after a catalyst ($NO_x$ purification catalyst) that purifies the nitrogen oxide in exhaust gas using ammonia. For example, when the ammonia concentration detection sensor of the present invention is disposed only in front of (upper stream) the $NO_x$ purification catalyst, it is preferable to dispose an $NO_x$ sensor capable of measuring the nitrogen oxide behind (lower stream) the $NO_x$ purification catalyst and to dispose a catalyst that purifies ammonia ($NH_3$ purification catalyst) before or behind (upper or lower stream) the $NO_x$ sensor. Thus, ammonia that has passed without reacting with the $NO_x$ purification catalyst is detoxicated with the $NH_3$ purification catalyst, and thus ammonia does not flow to the outside. By measuring the ammonia concentration before the $NO_x$ purification catalyst and measuring the $NO_x$ concentration behind the $NO_x$ purification catalyst, the used amount of ammonia in the $NO_x$ purification catalyst can be defined. In contrast, when the ammonia concentration detection sensor of the present invention is disposed before and behind the $NO_x$ purification catalyst, the used amount of ammonia in the $NO_x$ purification catalyst can be defined by measuring the ammonia concentration of both the ammonia concentration detection sensors. Preferable examples of systems to which the ammonia concentration detection sensor of the present invention is applied include an SCR system (SCR is the abbreviation for selective catalytic reduction). In this system, the $NO_x$ purification catalyst is disposed that reduces and purifies nitrogen oxides in exhaust gas from diesel engines using ammonia generated from an aqueous urea solution. Then, it is preferable to dispose the ammonia concentration detection sensor of the present invention at a downstream of the $NO_x$ purification catalyst to measure the exhaust gas after passing the $NO_x$ purification catalyst as the measurement target gas. Since the exhaust gas from diesel engines has a high temperature and contains a large amount of oxygen, the deterioration of the protective cover is likely to proceed. Thus, applying the present invention is highly significant.

BRIEF DESCRIPTION OF DRAWINGS

FIG. 5 is a view schematically illustrating the structure of a burner testing device 500.

BEST MODES FOR CARRYING OUT THE INVENTION

Figure 1:
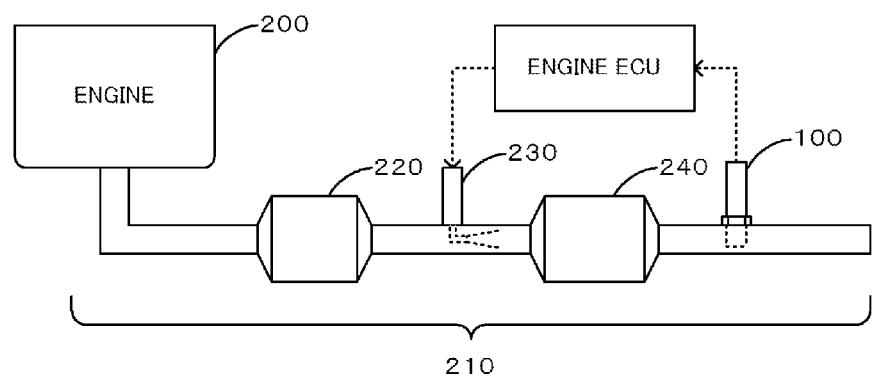
FIG. 1 is a view schematically illustrating an exhaust path 210 of an engine 200.
Figure 2:
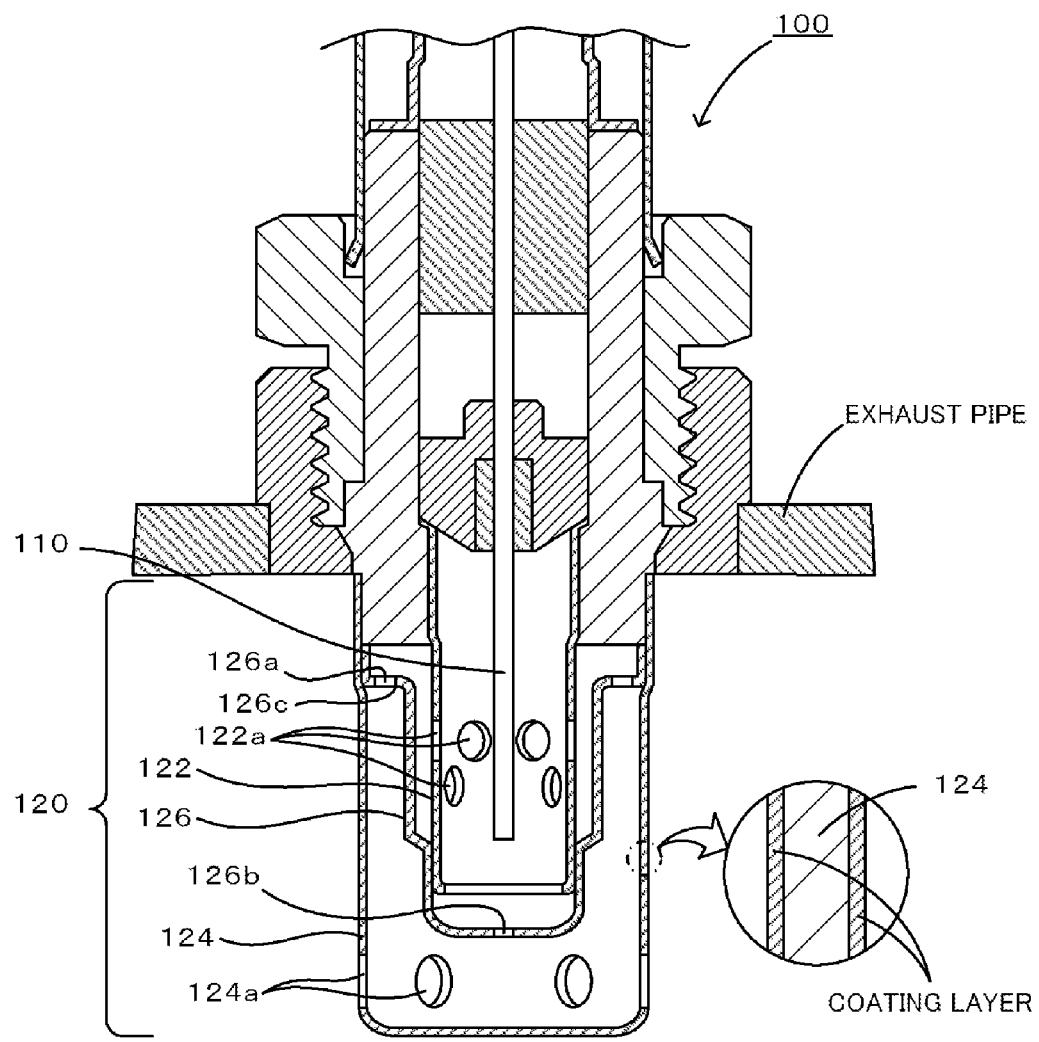
FIG. 2 is a longitudinal cross sectional view illustrating the structure of an ammonia concentration detection sensor 100.
Figure 3:
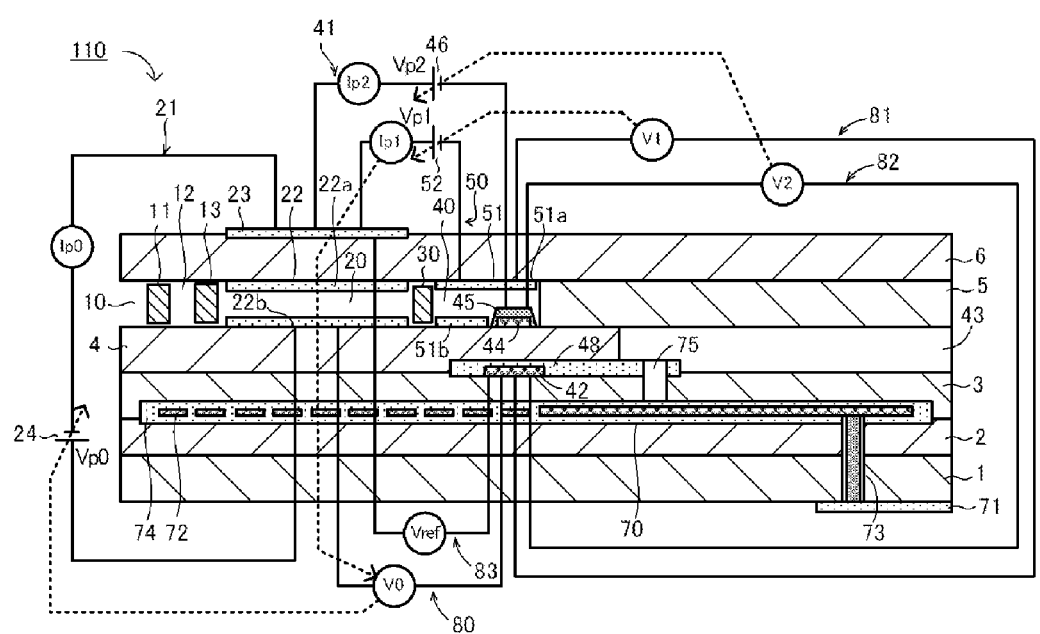
FIG. 3 is a cross sectional view illustrating the structure of a sensor element 110.

Next, the embodiments of the present invention will be described with reference to the drawings. FIG. 1 is a view schematically illustrating an exhaust path 210 of an engine 200. FIG. 2 is a longitudinal cross sectional view illustrating the structure of an ammonia concentration detection sensor 100. FIG. 3 is a cross sectional view illustrating the structure of a sensor element 110.

As shown in FIG. 1, the exhaust path 210 of the engine 200 is provided with an oxidation catalyst 220, an injector 230 that injects urea into an exhaust pipe, an SCR catalyst 240 that reduces a nitrogen oxide ($NO_x$) utilizing ammonia generating when urea hydrolyzes to decompose the same into harmless $N_2$ and $H_2O$, and an ammonia concentration detection sensor 100 that detects the concentration of excessive ammonia contained in exhaust gas after passing the SCR CATALYST 240. The exhaust gas immediately after being discharged from the engine 200 contains hydrocarbon (HC), carbon monoxide (CO), $NO_x$, and the like. In the exhaust gas, HC or CO is converted to water and carbon dioxide to be detoxified when passing the oxidation catalyst 220. However, $NO_x$ is still left even after passing the oxidation catalyst. The SCR CATALYST 240 reduces the $NO_x$ in the exhaust gas after passing the oxidation catalyst 220 utilizing ammonia generating when the urea injected from the injector 230 is hydrolyzed, and decompose the same into nonpoisonous $N_2$ and $H_2O$. The ammonia concentration detection sensor 100 detects the concentration of excessive ammonia contained in the exhaust gas after passing the SCR CATALYST 240. An engine ECU controls the amount of urea to be injected from the injector 230 to the exhaust pipe so that the detected excessive ammonia concentration comes close to zero.

As shown in FIG. 2, the ammonia concentration detection sensor 100 is provided with a sensor element 110 having a function of converting ammonia to $NO_x$ and a function of detecting the $NO_x$ after conversion and a protective cover 120 that protects the sensor element 110. Hereinafter, the sensor element 110 and the protective cover 120 will be described in detail.

First, the sensor element 110 will be described. As shown in FIG. 3, the sensor element 110 is a long and narrow plate-like element having a structure such that six layers of a first substrate layer 1, a second substrate layer 2, a third substrate layer 3, a first solid electrolyte layer 4, a spacer layer 5, and a second solid electrolyte layer 6, each containing an oxygen ion conductive solid electrolyte layer, such as zirconia ($ZrO_2$), are laminated in this order from the bottom in FIG. 3. The solid electrolyte forming the six layers is dense and airtight. The sensor element 110 is produced by, for example, subjecting ceramic green sheets each corresponding to each layer to a given processing, printing of a circuit pattern, and the like, laminating the ceramic green sheets, and firing the same for integrating.

In a space between the lower surface of the second solid electrolyte layer 6 and the upper surface of the first solid electrolyte layer 4, which is one tip portion of the sensor element 110, a gas introduction port 10, a first diffusion controlling unit 11, a buffer space 12, a second diffusion controlling unit 13, a first inner space 20, a third diffusion controlling unit 30, and a second inner space 40 are formed to be adjacent to each other in such a manner as to communicate with each other in this order. The gas introduction port 10, the buffer space 12, the first inner space 20, and the second inner space 40 are spaces inside the sensor element 110 in which the upper portion formed by cutting the spacer layer 5 is divided by the lower surface of the second solid electrolyte layer 6, the lower portion is divided by the upper surface of the first solid electrolyte layer 4, and the side is divided by the side surface of the spacer layer 5. The first diffusion controlling unit 11, the second diffusion controlling unit 13, and the third diffusion controlling unit 30 each are formed as two oblong (a direction perpendicular to the drawing is in agreement with the longitudinal direction of an opening) slits. A region from the gas introduction port 10 to the second inner space 40 is also referred to as a gas circulation portion.

At a position distant from the tip portion relative to the gas circulation portion, a standard gas introduction space 43 is provided in a place between the upper surface of the third substrate layer 3 and the lower surface of the spacer layer 5 in which the side is divided by the side surface of the first solid electrolyte layer 4. Into the standard gas introduction space 43, the air, for example, is introduced as a standard gas for measuring the $NO_x$ concentration. An air introduction layer 48 is a layer formed of porous alumina. Into the air introduction layer 48, a standard gas is introduced through the standard gas introduction space 43. The air introduction layer 48 is formed to cover the reference electrode 42. The reference electrode 42 is an electrode formed in such a manner as to be interposed between the upper surface of the third substrate layer 3 and the first solid electrolyte layer 4, and, as described above, the air introduction layer 48 to be connected to the standard gas introduction space 43 is formed around the reference electrode. As described later, the oxygen concentration (oxygen partial pressure) in the first inner space 20 and the second inner space 40 can be measured using the reference electrode 42.

In the gas circulation portion, the gas introduction port 10 opens to the exterior space. Therefore, a measurement target gas is taken into the sensor element 110 from the exterior space through the gas introduction port 10. The first diffusion controlling unit 11 is a portion that applies a given diffusion resistance to the measurement target gas taken from the gas introduction port 10. The buffer space 12 is a space provided for guiding the measurement target gas introduced from the first diffusion controlling unit 11 to the second diffusion controlling unit 13. The second diffusion controlling unit 13 is a portion that applies a given diffusion resistance to the measurement target gas to be introduced into the first inner space 20 from the buffer spice 12. When the measurement target gas is introduced into the first inner space 20 from the outside of the sensor element 110, the measurement target gas rapidly taken into the sensor element 110 from the gas introduction port 10 by pressure fluctuation (exhaust pulsation in the case where the measurement target gas is exhaust gas of automobiles) of the measurement target gas in the exterior space is not directly introduced into the first inner space 20 but introduced into the first inner space 20 after the concentration fluctuation of the measurement target gas is cancelled through the first diffusion controlling unit 11, the buffer space 12, and the second diffusion controlling unit 13. Thus, the concentration fluctuation of the measurement target gas to be introduced into the first inner space 20 becomes negligible.

The first inner space 20 is formed as a space for oxidizing ammonia in the measurement target gas introduced through the second diffusion controlling unit 13 with oxygen in the measurement target gas to convert the same to $NO_x$ and adjusting the oxygen partial pressure. The oxygen partial pressure is adjusted by the operation of a main pump cell 21. The main pump cell 21 is an electrochemical pump cell constituted by an inner pump electrode 22 having a ceiling electrode portion 22a provided on the approximately entire surface of the lower surface of the second solid electrolyte layer 6 facing the first inner space 20, an outer pump electrode 23 provided in such a manner to be exposed to the exterior space in a region corresponding to the ceiling electrode portion 22a, and the second solid electrolyte layer 6 interposed between these electrodes. The inner pump electrode 22 is formed crossing the upper and lower solid electrolyte layers (the second solid electrolyte layer 6 and the first solid electrolyte layer 4) dividing the first inner space 20 and the spacer layer 5 giving a side wall. Specifically, the inner pump electrode 22 is disposed in a structure such that the ceiling electrode portion 22a is formed on the lower surface of the second solid electrolyte layer 6 giving the ceiling surface of the first inner space 20, a bottom electrode portion 22b is formed on the upper surface of the first solid electrolyte layer 4 giving the bottom surface, and a side electrode portion (not shown) is formed on the side wall surface (inner surface) of the spacer layer 5 constituting both side walls of the first inner space 20 in such a manner as to connect the ceiling electrode portion 22a and the bottom electrode portion 22b, so that a tunnel shape is formed at a portion where the side electrode portion is disposed. The inner pump electrode 22 and the outer pump electrode 23 are formed as porous cermet electrodes (e.g., cermet electrode of Pt and $ZrO_2$ containing 1% of Au). The inner pump electrode 22 contacting the measurement target gas is formed using materials whose reduction ability to the $NO_x$ ingredients in the measurement target gas is reduced.

In the main pump cell 21, a desired pump voltage Vp0 is applied between the inner pump electrode 22 and the outer pump electrode 23 to flow a pump current Ip0 in the positive or negative direction between the inner pump electrode 22 and the outer pump electrode 23, thereby pumping out oxygen in the first inner space 20 to the exterior space or pumping oxygen in the exterior space into the first inner space 20.

In order to detect the oxygen concentration (oxygen partial pressure) in the atmosphere in the first inner space 20, an electrochemical sensor cell, i.e., an oxygen partial pressure detection sensor cell 80 for controlling the main pump is constituted by the inner pump electrode 22, the second solid electrolyte 6, the spacer layer 5, the first solid electrolyte layer 4, the third substrate layer 3, and the reference electrode 42. The oxygen concentration (oxygen partial pressure) in the first inner space 20 can be found out by measuring the electromotive force V0 in the oxygen partial pressure detection sensor cell 80. Furthermore, the pump current Ip0 is controlled by performing feedback control of the Vp0 so that the electromotive force V0 is fixed. Thus, the oxygen concentration in the first inner space 20 can be maintained at a given fixed value.

The second inner space 40 is provided as a space for performing treatment relating to the measurement of the $NO_x$ concentration in the measurement target gas introduced through the third diffusion controlling unit 30. The third diffusion controlling unit 30 is a portion that gives a given diffusion resistance to the measurement target gas whose oxygen concentration (oxygen partial pressure) is controlled by the action of the main pump cell 21 in the first inner space 20 to guide the measurement target gas to the second inner space 40. The $NO_x$ concentration is measured mainly by the action a measurement pump cell 41 in the second inner space 40 in which the oxygen concentration is adjusted by an auxiliary pump cell 50.

In the second inner space 40, the oxygen concentration (oxygen partial pressure) is adjusted in advance in the first inner space 20, and then the oxygen partial pressure of the measurement target gas introduced through the third diffusion controlling unit 30 is adjusted by the auxiliary pump cell 50. Thus, the oxygen concentration in the second inner space 40 can be maintained at a constant level with high accuracy, and thus high-accuracy $NO_x$ concentration measurement can be achieved.

The auxiliary pump cell 50 is an auxiliary electrochemical pump cell constituted by an auxiliary pump electrode 51 having a ceiling electrode portion 51a provided on the approximately entire surface of the lower surface of the second solid electrolyte layer 6 facing the second inner space 40, the outer pump electrode 23 (which is not limited to the outer pump electrode 23, and a suitable outer electrode outside the sensor element 110 may suffice), and the second solid electrolyte layer 6. The auxiliary pump electrode 51 is disposed in the second inner space 40 in the same tunnel-shaped structure as that of the inner pump electrode 22 provided in the first inner space 20. More specifically, a tunnel-shaped structure is achieved in which the ceiling electrode portion 51a is formed on the second solid electrolyte layer 6 giving the ceiling surface of the second inner space 40, a bottom electrode portion 51b is formed on the first solid electrolyte layer 4 giving the bottom surface of the second inner space 40, and a side electrode portion (not shown) connecting the ceiling electrode portion 51a and the bottom electrode portion 51b is formed on each wall surface of the spacer layer 5 giving the side wall of the second inner space 40. The auxiliary pump electrode 51 is formed using materials whose reduction ability to the $NO_x$ ingredients in the measurement target gas is reduced in the same manner as in the inner pump electrode 22.

In the auxiliary pump cell 50, by applying a desired pump voltage Vp1 between the auxiliary pump electrode 51 and the outer pump electrode 23, oxygen in the atmosphere in the second inner space 40 can be pumped out to the exterior space or can be pumped into the second inner space 40 from the exterior space.

In order to control the oxygen partial pressure in the atmosphere in the second inner space 40, an electrochemical sensor cell, i.e., an oxygen partial pressure detection sensor cell 81 for controlling the auxiliary pump, is constituted by the auxiliary pump electrode 51, the reference electrode 42, the second solid electrolyte layer 6, the spacer layer 5, the first solid electrolyte layer 4, and the third substrate layer 3. In a variable power source 52 that is voltage controlled based on the electromotive force V1 detected by the oxygen partial pressure detection sensor cell 81, the auxiliary pump cell 50 performs pumping. Thus, the oxygen partial pressure in the atmosphere in the second inner space 40 is controlled to a low partial pressure by which the $NO_x$ measurement is not substantially affected. Moreover, in addition thereto, a pump current Ip1 of the auxiliary pump cell 50 is used for controlling the electromotive force of the oxygen partial pressure detection sensor cell 80 for controlling the main pump. Specifically, the pump current Ip1 is inputted as a control signal to the oxygen partial pressure detection sensor cell 80 to control the electromotive force V0, whereby the gradient of the oxygen partial pressure in the measurement target gas to be introduced into the second inner space 40 from the third diffusion controlling unit 30 is controlled to be always fixed. When used as an $NO_x$ sensor, the oxygen concentration in the second inner space 40 is maintained at a fixed value of about 0.001 ppm by the action of the main pump cell 21 and the auxiliary pump cell 50.

The measurement pump cell 41 measures the $NO_x$ concentration in the measurement target gas in the second inner space 40. The measurement pump cell 41 is an electrochemical pump cell constituted by a measurement electrode 44 provided on the upper surface of the first solid electrolyte layer 4 facing the second inner space 40 and at a position apart from the third diffusion controlling unit 30, the outer pump electrode 23, the second solid electrolyte layer 6, the spacer layer 5, and the first solid electrolyte layer 4. The measurement electrode 44 is a substantially rectangular porous cermet electrode as viewed in plane view. The measurement electrode 44 also functions as an $NO_x$ reduction catalyst that reduces $NO_x$ present in the atmosphere in the second inner space 40. The measurement electrode 44 is coated with a fourth diffusion controlling unit 45. The fourth diffusion controlling unit 45 is a film constituted by a porous body containing alumina ($Al_2O_3$) as the main ingredients. The fourth diffusion controlling unit 45 has a function of limiting the amount of $NO_x$ flowing into the measurement electrode 44 and also has a function as a protective film of the measurement electrode 44.

In the measurement pump cell 41, the oxygen generated by the decomposition of $NO_x$ in the atmosphere around the measurement electrode 44 is pumped out, and the generation amount can be detected as a pump current Ip2.

In order to detect the oxygen partial pressure around the measurement electrode 44, an electrochemical sensor cell, i.e., an oxygen partial pressure detection sensor cell 82 for controlling the measurement pump, is constituted by the second solid electrolyte layer 6, the spacer layer 5, the first solid electrolyte layer 4, the third substrate layer 3, the measurement electrode 44, and the reference electrode 42. A variable power source 46 is controlled based on the electromotive force V2 detected by the oxygen partial pressure detection sensor cell 82 for controlling the measurement pump.

The measurement target gas guided into the second inner space 40 reaches the measurement electrode 44 through the fourth diffusion controlling unit 45 under the situation where the oxygen partial pressure is controlled. $NO_x$ in the measurement target gas around the measurement electrode 44 is reduced ($2NO \rightarrow N_2 + O_2$) to generate oxygen. The generated oxygen is pumped by the measurement pump cell 41. In the process, the voltage Vp2 of the variable power source is controlled so that the control voltage V2 detected by the oxygen partial pressure detection sensor cell 82 for controlling the measurement pump is fixed. Since the amount of the oxygen generating around the measurement electrode 44 is in proportional to the $NO_x$ concentration in the measurement target gas, the $NO_x$ concentration in the measurement target gas is calculated using the pump current Ip2 in the measurement pump cell 41. Here, the measurement target gas before introduced into the ammonia concentration detection sensor 100 does not contain $NO_x$ because $NO_x$ is reduced and detoxified by the SCR CATALYST 240. However, excessive ammonia is contained, and the ammonia is oxidized in the first inner space 20 to be converted to $NO_x$, resulting in the fact that $NO_x$ derived from ammonia is contained in the measurement target gas introduced into the second inner space 40. Therefore, the ammonia concentration can be derived by measuring the $NO_x$ concentration. A specific procedure for deriving the ammonia concentration is as follows. More specifically, the pump current Ip2 when a sample gas containing no ammonia or $NO_x$ is made to flow beforehand is defined as an offset current, the pump current difference ΔIp2 obtained by subtracting the offset current from the pump current Ip2 when an actual measurement target gas is made to flow, and then $NO_x$ concentration, i.e., the ammonia concentration, is calculated from the oxygen amount corresponding to the pump current difference ΔIp2.

When an oxygen partial pressure detection measure is constituted as an electrochemical sensor cell by combining the measurement electrode 44, the first solid electrolyte layer 4, the third substrate layer 3, and the reference electrode 42, the electromotive force depending on the difference between the amount of the oxygen generated by the reduction of the $NO_x$ ingredients in the atmosphere around the measurement electrode 44 and the amount of the oxygen contained in the standard atmosphere can be detected. Thus, the concentration of the $NO_x$ ingredients in the measurement target gas can also be determined. An electrochemical sensor cell 83 is constituted by the second solid electrolyte layer 6, the spacer layer 5, the first solid electrolyte layer 4, the third substrate layer 3, the outer pump electrode 23, and the reference electrode 42, in which the oxygen partial pressure in the measurement target gas outside the sensor can be detected by the electromotive force Vref obtained by the sensor cell 83.

In the ammonia concentration detection sensor 100 thus structured, the measurement target gas in which the oxygen partial pressure is always maintained at a low fixed value (value that does not substantially have influence on the NOx measurement) is given to the measurement pump cell 41 by operating the main pump cell 21 and the auxiliary pump cell 50. Therefore, the $NO_x$ concentration in the measurement target gas can be found based on the pump current Ip2 that flows by pumping out the oxygen generated by the reduction of $NO_x$ from the measurement pump cell 41 approximately in proportion to the $NO_x$ concentration in the measurement target gas.

The sensor element 110 is further provided with a heater unit 70 having a temperature adjusting function for heating and warming the sensor element 110 in order to increase the oxygen ion conductivity of the solid electrolytes. The heater unit 70 is provided with a heater electrode 71, a heater 72, a through hole 73, a heater insulating layer 74, and a pressure diffusion hole 75. The heater electrode 71 is an electrode formed in such a manner as to be in contact with the lower surface of the first substrate layer 1. By connecting the heater electrode 71 to an external power supply, electric power can be supplied to the heater unit 70 from the outside. The heater 72 is an electrical resistance formed in such a manner as to be interposed between the second substrate layer 2 and the third substrate layer 3 from the upper and lower sides. The heater 72 is connected to the heater electrode 71 via the through hole 73 and generates heat by receiving electric power from the outside via the heater electrode 71 to heat and warm the solid electrolytes forming the sensor element 110. The heater 72 is embedded throughout the region from the first inner space 20 to the second inner space 40, and can adjust the temperature of the whole ammonia concentration detection sensor 100 to a temperature at which the solid electrolytes are activated. The heater insulating layer 74 is an insulating layer formed with an insulator, such as alumina, on the upper and lower surfaces of the heater 72. The heater insulating layer 74 is formed in order to achieve electrical insulation between the second substrate layer 2 and the heater 72 and the electrical insulation between the third substrate layer 3 and the heater 72.

The pressure diffusion hole 75 is a portion provided in such a manner as to penetrate the third substrate layer 3 to communicate with the standard gas introduction space 43 and is formed in order to relieve an increase in the internal pressure with an increase in the temperature inside the heater insulating layer 74.

Next, the protective cover 120 will be described. As shown in FIG. 2, the protective cover 120 is disposed in such a manner as to surround the circumference of the sensor element 110. The protective cover 120 has an inner protective cover 122 that covers the tip of the sensor element 110, an outer protective cover 124 that covers the inner protective cover 122, and an intermediate protective cover 126 disposed between the inner protective cover 122 and the outer protective cover 124. The inner protective cover 122 is formed into a cylindrical shape, and a plurality of inner protective cover holes 122a are formed at a position facing the sensor element 110. The outer protective cover 124 is formed into a cylindrical shape having a bottom and outer protective cover holes 124a are formed at a position not facing the inner protective cover 122 of the side surfaces. The intermediate protective cover 126 is formed into a cylindrical shape having a bottom having a level difference (flange portion 126c) in the middle of the axis direction, and abuts against the outer circumferential surface of the inner protective cover 122 at the tip side and abuts against the inner circumferential surface of the outer protective cover 124 at the rear end side relative to the flange portion 126c. At the flange portion 126c, a plurality (e.g., six pieces) of circular (crescent-shaped) slits 126a centering on the axis of the intermediate protective cover 126 are formed at equal intervals. The intermediate protective cover 126 has an intermediate protective cover hole 126b formed at the tip side.

Each of the protective covers 122, 124, and 126 is processed with a stainless steel plate, and the front and back surfaces thereof are coated with a coating layer (in the circle of FIG. 2) by CVD. The coating material is not particularly limited insofar as it can prevent the deterioration of stainless steel. For example, the coating material is a nitride, a carbide, or a carbonitride of metal elements, and may contain at least one member selected from the group consisting of Ti, Zr, and Cr as the metal elements. The coating material is preferably hydrophobic. As such a coating material, TiC, TiCN, TiN, ZrC, ZrCN, ZrN, CrC, CrCN, CrN, TiAlN, ZrAlN, CrAlN, and the like are mentioned. The coating material preferably has a heat resistant temperature of 400° C. or higher. Although DLC (diamond-like carbon) is hydrophilic, DLC may be used as the coating material.

According to the embodiments described in detail above, since the protective cover 120 is coated with the coating layer, the protective cover 120 is hard to deteriorate even when exposed to an oxidative gas or a corrosive gas over a long period of time. Accordingly, even when the ammonia concentration detection sensor 100 is used over a long period of time, the ammonia concentration detection sensitivity is hard to decrease. When combustion gas contains $H_2O$, condensation water is generated in the exhaust gas path after stopping combustion, and is scattered immediately after starting combustion to apply damages to the sensor element 110 of the ammonia concentration detection sensor 100 disposed therebehind in some cases. However, when the coating layer is hydrophobic, water may be difficult to adhere to the protective cover 120, and thus the formation of cracks can be prevented due to the adhesion of water to the sensor element 110. As the reasons therefor, it is considered that the introduction of water into the system is prevented because the coating layer is hydrophobic. Furthermore, since the exhaust gas from diesel engines has a high temperature and contains a large amount of oxygen, the deterioration of the protective cover 120 is likely to proceed. Thus, applying the present invention is highly significant.

It is a matter of course that the present invention is not limited to the Embodiments described above at all and can be carried out in various aspects insofar as the aspects are within the technical scope of the present invention.

For example, in the Embodiments, described above, although the ammonia in the measurement target gas to be introduced into the ammonia concentration detection sensor 100 is converted to $NO_x$ in the first inner space 20, the ammonia may be oxidized by residual oxygen in the second inner space 40 and converted to $NO_x$ in place of converting the ammonia to $NO_x$ in the first inner space 20. Or, the ammonia concentration may be determined by decomposing ammonia in the second inner space 40 to generate $H_2$ and $N_2$, pumping out $H_2$ of the $H_2$ and $N_2$ with a proton pump (Paragraphs 0103 and 0104 of U.S. Pat. No. 3,511,468), and detecting the pump current when pumping out.

In the Embodiments described above, although the protective cover 120 is used that has a three-layer structure of the inner protective cover 122, the outer protective cover 124, and the intermediate protective cover 126. The protective cover 120 may have as two-layer structure or a single layer structure.

In the Embodiments described above, although the coating layer is formed on both the front and back surfaces of each of the protective covers 122, 124, and 126, the coating layer may be formed on either one of the front and back surfaces or the coating layer may be formed on any one or two of the protective covers 122, 124, and 126.

In the Embodiments described above, although the coating layer is formed by CVD, the coating layer may be formed by PVD, spraying, or the like.

EXAMPLES

Examples 1 to 8 and Comparative Example 1

A sensor having the same structure as that of the ammonia concentration detection sensor 100 described above except that the coating layer of the protective cover 120 was not formed was used as Comparative Example 1. Sensors in which a coating layer was formed by CVD using various coating materials on the protective cover 120 of the sensor of Comparative Example 1 were used as Examples 1 to 8. The base materials, the coating materials, and the heat resistant temperature (according to a differential thermal balance (TG-DTA)) of the coating materials of the protective cover 120 are as shown in Table 1. Among the coating materials, DLC is hydrophilic and others are hydrophobic.

Examples 1 to 8 and Comparative Example 1 were measured for an $NH_3$ sensitivity reduction rate D (%) before and after a durability test and a breakage-starting water amount W ($cm^3$). The results are shown in Table 1.

TABLE 1

| | PROTECTIVE COVER | | | D(%)*1 | | |
|---|---|---|---|---|---|---|
| | BASE MATERIAL | COATING MATERIAL | HEAT RESISTANT TEMPERATURE OF COATING MATERIAL (° C.) | $\lambda = 1.05 \pm 0.05$ | $\lambda = 0.95 \pm 0.05$ | W($cm^3$)*2 |
| COMPARATIVE EXAMPLE 1 | SUS310S | — | — | 40 | 43 | 100 |
| EXAMPLE 1 | SUS310S | DLC | 200 | 37 | 38 | — |
| EXAMPLE 2 | SUS310S | TiC | 400 | 30 | 30 | — |
| EXAMPLE 3 | SUS310S | TiCN | 450 | 28 | 28 | — |
| EXAMPLE 4 | SUS310S | TiN | 550 | 23 | 24 | — |
| EXAMPLE 5 | SUS310S | ZrN | 700 | 17 | 18 | — |
| EXAMPLE 6 | SUS310S | CrC | 750 | 12 | 13 | — |
| EXAMPLE 7 | SUS310S | TiAlN | 1100 | 7 | 8 | 130 |
| EXAMPLE 8 | SUS310S | CrN | 1100 | 2 | 3 | 140 |

*1 D(%) represents $NH_3$ sensitivity reduction rate obtained by the equation below.

$$D(\%) = \frac{\text{pre-durability test } \Delta Ip2 - \text{post-durability test } \Delta Ip2}{\text{pre-surability test } \Delta Ip2} \times 100$$

*2 W($cm^3$) represents a breakage-starting water amount.

Figure 4:
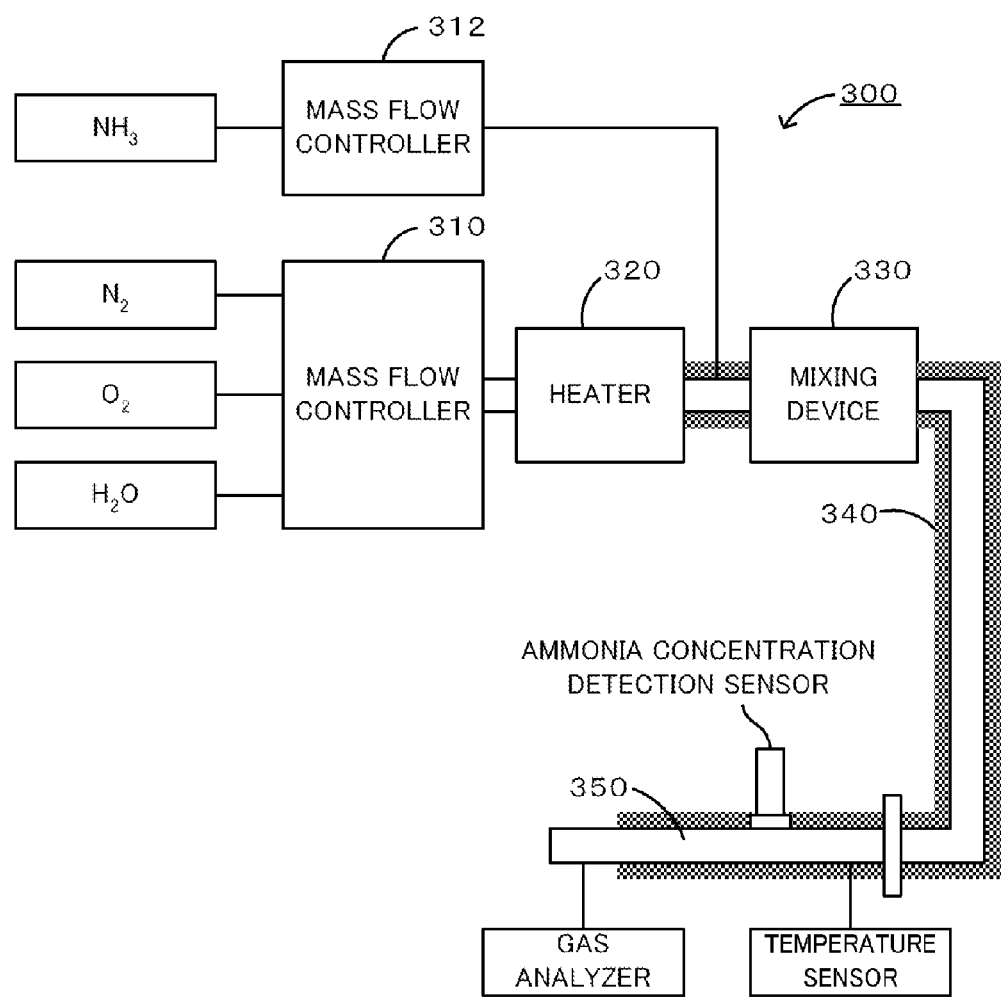
FIG. 4 is a view schematically illustrating the structure of an analysis system 300.

The $NH_3$ sensitivity reduction rate D (%) was determined using an analysis system 300 shown in FIG. 4. More specifically, the analysis system 300 was provided with a mass flow controller (SEC-Z500 series manufactured by Horiba S-Tec) 310 that adjusts the flow rate of $N_2$ gas, $O_2$ gas, and vapor, a heater 320 connected to the mass flow controller 310, and a mixing device 330 that mixes gas passing the heater 320 and $NH_3$ gas having adjusted flow rate to be supplied from the mass flow controller 312, in which a heat insulating pipe 340 coated with a heat insulating material was connected to the downstream of the heater 320 and a measurement pipe 350 attached to a temperature sensor, an ammonia concentration detection sensor, and a gas analyzer was connected to the downstream of the heat insulating pipe 340. In the drawings, shading portions represent the heat insulating materials. The ammonia concentration detection sensors of Examples 1 to 8 and Comparative Example 1 were measured for the pump current difference ΔIp2 before a durability test. Then, the durability test was performed. Then, the pump current difference ΔIp2 was measured again after the durability test. Here, the pump current difference ΔIp2 is a value obtained by subtracting a pump current Ip2 (offset current) when $N_2$ gas containing no $NH_3$ was used from a pump current Ip2 when $N_2$ gas containing 100 ppm of $NH_3$ was used. The specific measurement conditions in this case are shown in Table 2. Then, the $NH_3$ sensitivity reduction rate D (%) was calculated by Equation represented in the margin of Table 1. The durability test was conducted using a burner testing device 500 shown in FIG. 5. FIG. 5 is a view schematically illustrating the structure of the burner testing device 500, where FIG. 5A is a front view and FIG. 5B is a side view of the burner testing device 500. The burner testing device is constructed to have a pipe 502 with three sensor mounts at the top and bottom respectively and four sensor mounts at both sides respectively for mounting a sensor, and to combust fuel by a burner 504 provided at one end of the device so as to flow the generated exhaust gas through the pipe 502. Specifically, the durability test was performed by mounting the ammonia concentration detection sensors to the sensor mounts, and flowing exhaust gas (gas temperature of 950° C.) when the engine was controlled so that λ was 1.05±0.05 using LPG as a fuel for 400 hours. The same test was performed by flowing exhaust gas (gas temperature of 950° C.) when the engine was controlled so that λ was 0.95±0.05 using LPG as a fuel for 400 hours. The results obtained by λ of 1.05±0.05 and λ of 0.95±0.05 are shown in Table 1.

TABLE 2

| Measurement Condition | |
|---|---|
| Gas temperature | 125° C. |
| Gas Flow Rate | 200 L/min |
| Base Gas | Nitrogen |
| $NH_3$ Concentration$^{\times 1}$ | 100 ppm(200 L/min) |
| $O_2$ COncentration$^{\times 1}$ | 0.5% |
| Moisture Content$^{\times 1}$ | 3% |

$^{\times 1}$ Determined in terms of volume.

Figure 6:
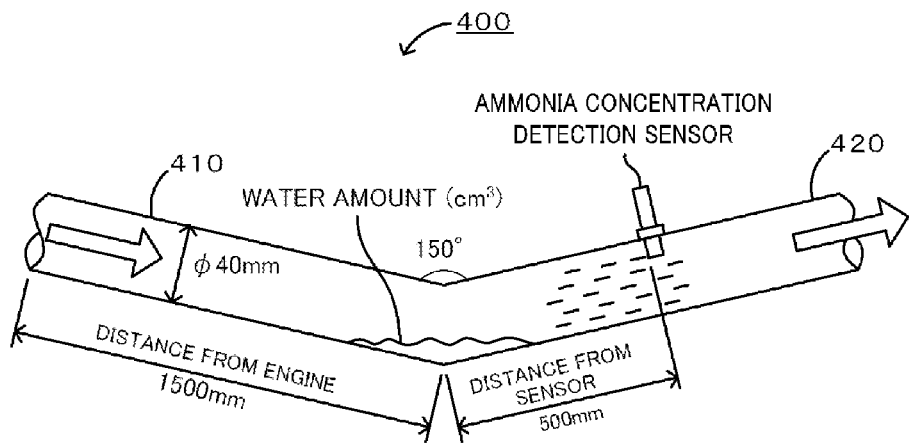
FIG. 6 is a view schematically illustrating a breakage-starting water amount measuring device 400.

In contrast, the breakage-starting water amount W ($cm^3$) was determined using a breakage-starting water amount measuring device 400 shown in FIG. 6. More specifically, as the breakage-starting water amount measuring device 400, a device was prepared in which two pipes 410 and 420 having a diameter of 40 mm were connected to each other so that the angle was 150°, the engine was connected to the position 1500 mm apart from the joint, and the ammonia concentration detection sensor before the durability test was disposed at the position 500 mm apart from the joint toward the side opposite to the engine. Then, the engine was operated under given operating conditions in a state where a suitable amount of water was stored in the joint. While operating the engine, the water in the joint was scattered toward the sensor, and all the water stored in the joint was discharged to the outside of the pipe. Thereafter, when abnormalities were observed in the outputs from the ammonia concentration detection sensor, the operation of the engine was stopped, and the amount of the water stored at the beginning of the test was defined as the breakage-starting water amount. When abnormalities were not observed in the sensor, the amount of water was increased to 10 $cm^3$, and then the same test was carried out until abnormalities were observed in the sensor. The given operating conditions were as follows: electrically charging of the heater of the ammonia concentration detection sensor was started, 60 seconds after, the engine was started (Number of rotations in an idling state=600 rpm), and 15 seconds after starting the engine, 3 second acceleration operation (Number of rotations at the peak in an acceleration state=5000 rpm) was continuously performed 3 times, which was defined as 1 cycle, and then the cycle was performed once.

As is clear from Table 1, in Examples 1 to 8, the $NH_3$ sensitivity reduction rate D became small compared with Comparative Example 1, regardless of whether λ was rich or lean, that is, fuel was rich or lean. The reasons therefor are imagined as follows. More specifically, it is considered that, in Examples 1 to 8, since the protective cover was coated with the coating layer, the protective cover did not deteriorate even after the durability test. In contrast, it is considered that, in Comparative Example 1, the protective cover was not coated with a coating layer, and thus the protective cover deteriorated by the durability test, and ammonia in a measurement target gas was decomposed by the protective cover deteriorating when passing the protective cover from the outside to the inside. When a coating material having a heat resistant temperature of 400° C. or higher, the $NH_3$ sensitivity reduction rate D became 30% or lower. When a coating material having a heat resistant temperature of 700° C. or higher was used, the $NH_3$ sensitivity reduction rate D became 20% or lower, and the suppression of the deterioration of the protective cover became noticeable. When a coating material having a heat resistant temperature of 1000° C. or higher was used, the $NH_3$ sensitivity reduction rate D became 10% or lower and the suppression of the deterioration of the protective cover became more noticeable.

In Examples 7 and 8, the breakage-starting water amount became large compared with Comparative Example 1. It is considered that this is because the coating materials of the protective covers of Examples 7 and 8 are hydrophobic. The breakage-starting water amount was not measured in Examples 2 to 6. However, since the coating materials thereof are hydrophobic similarly as in Examples 7 and 8, it is estimated that the breakage-starting water amount becomes large compared with Comparative Example 1.

Figure 7:
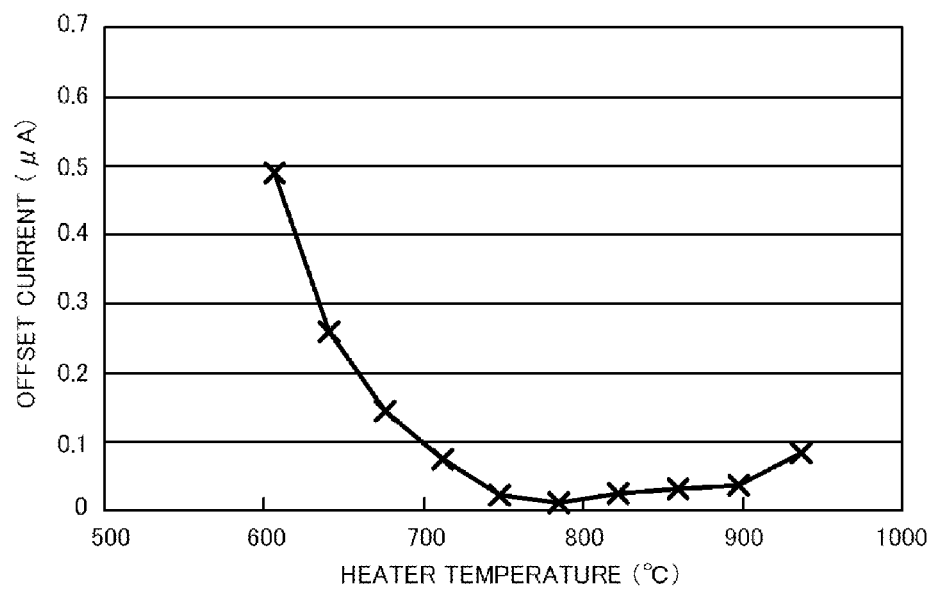
FIG. 7 is a graph illustrating the relationship between a heater temperature and an offset current.
Figure 8:
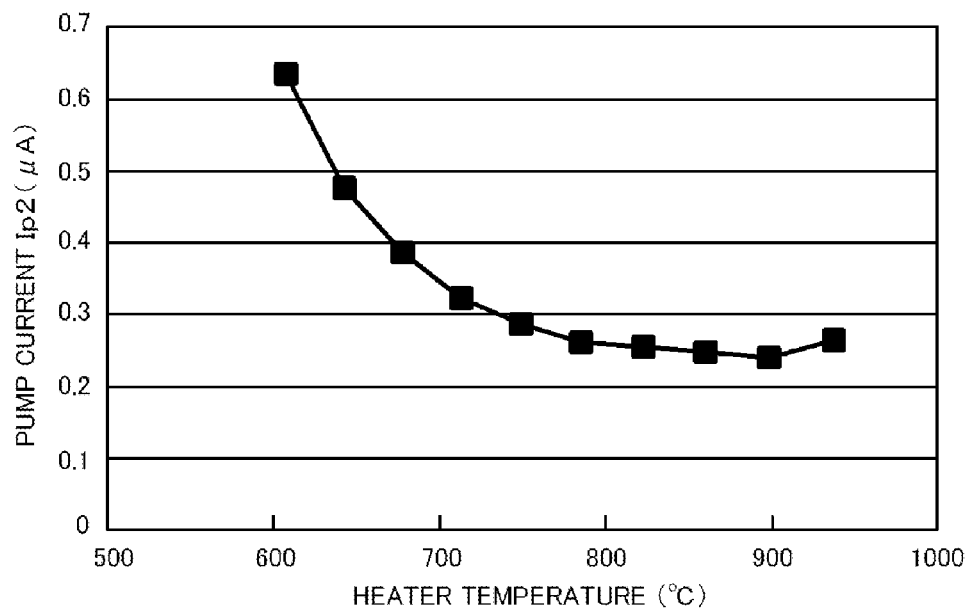
FIG. 8 is a graph illustrating the relationship between a heater temperature and a pump current Ip2.
Figure 9:
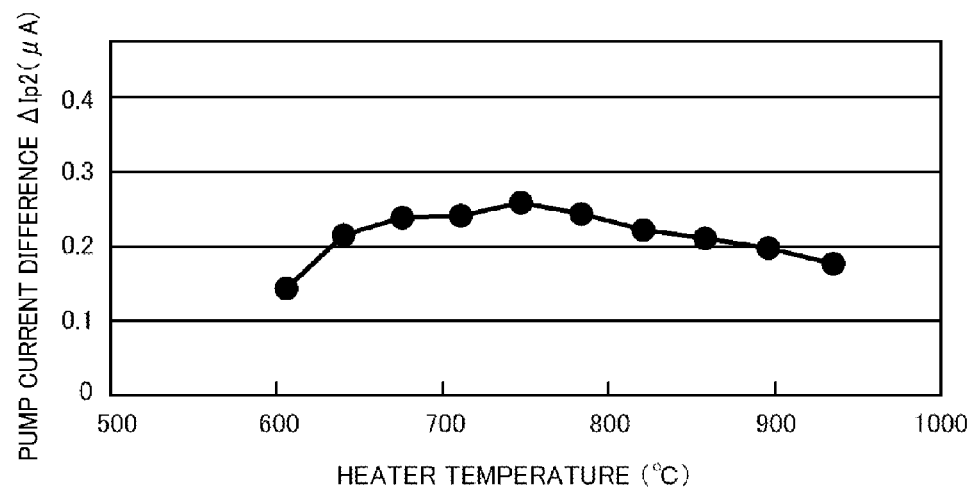
FIG. 9 is a graph illustrating the relationship between a heater temperature and a pump current difference ΔIp2.

Next, the ammonia concentration detection sensor of Example 8 was used for analyzing changes in the offset current, pump current Ip2, and pump current difference ΔIp2 depending on the heater temperature. Each current value was measured under the same conditions for measuring the offset current, pump current Ip2, and pump current difference ΔIp2 before the durability test when the $NH_3$ sensitivity reduction rate D (%) was calculated. The results are shown in FIGS. 7 to 9. As is clear from FIGS. 7 to 9, when the heater temperature was 750° C. or higher and 850° C. or lower, the offset current was very small and the value of the pump current difference ΔIp2 was also relatively large. However, when the heater temperature was lower than 750° C. or exceeded 850° C., the offset current becomes large, the sensitivity is likely to decrease, and the electrodes 22 and 51 are likely to deteriorate. Thus, such a heater temperature is not preferable.

The present application claims priorities from Japanese Patent Application No. 2009-169292 filed on Jul. 17, 2009, and the Japanese Patent Application No. 2010-155899 filed on Jul. 8, 2010, the entire contents of both of which are incorporated herein by reference.

What is claimed is:

1. An ammonia concentration detection sensor, comprising:
 a sensor element capable of detecting an ammonia concentration of a measurement target gas; and
 a protective cover that regulates inflow of the measurement target gas to the sensor element and protects the sensor element,
 wherein the protective cover is formed of stainless steel and is coated with a coating layer that contains a nitride, a carbide, or a carbonitride of a metal element and contains at least one member selected from the group consisting of Ti, Zr, and Cr as the metal element, and
 wherein the coating layer has a heat resistant temperature at least 1000° C.

2. The ammonia concentration detection sensor according to claim 1, being disposed, in an exhaust system in which a nitrogen oxide is generated, at least one of before and after a catalyst that uses ammonia to purify the nitrogen oxide in exhaust gas.

3. The ammonia concentration detection sensor according to claim 1, wherein the coating material is one of TiAlN and CrN.

* * * * *